(12) United States Patent
Hursan et al.

(10) Patent No.: US 7,298,142 B2
(45) Date of Patent: Nov. 20, 2007

(54) METHOD AND APPARATUS FOR RESERVOIR FLUID CHARACTERIZATION IN NUCLEAR MAGNETIC RESONANCE LOGGING

(75) Inventors: Gabor G. Hursan, The Woodlands, TX (US); Songhua Chen, Katy, TX (US)

(73) Assignee: Baker Hughes Incorporated, Houston, TX (US)

( * ) Notice: Subject to any disclaimer, the term of this patent is extended or adjusted under 35 U.S.C. 154(b) by 17 days.

(21) Appl. No.: 11/167,323

(22) Filed: Jun. 27, 2005

(65) Prior Publication Data

US 2006/0290350 A1 Dec. 28, 2006

(51) Int. Cl.
*G01V 3/00* (2006.01)
*G01R 33/20* (2006.01)
(52) U.S. Cl. .................. 324/303; 324/306; 324/318
(58) Field of Classification Search .............. None
See application file for complete search history.

(56) References Cited

U.S. PATENT DOCUMENTS

| | | | |
|---|---|---|---|
| 5,023,551 A | 6/1991 | Kleinberg et al. | 324/303 |
| 5,291,137 A | 3/1994 | Freedman | 324/303 |
| 5,486,762 A | 1/1996 | Freedman et al. | 324/303 |
| 5,498,960 A | 3/1996 | Vinegar et al. | 324/303 |
| 5,680,043 A | 10/1997 | Hurlimann et al. | 324/303 |
| 6,032,101 A | 2/2000 | Freedman et al. | 702/8 |
| 6,331,775 B1 | 12/2001 | Thern et al. | 324/303 |
| 6,392,409 B1 | 5/2002 | Chen | 324/303 |
| 6,600,316 B2 | 7/2003 | Chen et al. | 324/303 |
| 6,714,009 B2 * | 3/2004 | Heidler | 324/303 |
| 2002/0149364 A1 | 10/2002 | Edwards | 324/307 |
| 2002/0153888 A1 | 10/2002 | Kruspe | 324/303 |
| 2002/0163334 A1 | 11/2002 | Hagiwara | 324/303 |
| 2002/0163335 A1 | 11/2002 | Prammer | 324/303 |
| 2002/0175682 A1 | 11/2002 | Chen | 324/303 |
| 2003/0001569 A1 | 1/2003 | Chen | 324/303 |
| 2003/0006766 A1 | 1/2003 | Kruspe | 324/303 |
| 2003/0006769 A1 | 1/2003 | Edwards | 324/303 |

(Continued)

OTHER PUBLICATIONS

PCT International Search Report for International Application No. PCT/US06/25004; International Filing Date of Jun. 22, 2006; Date of Mailing Jun. 8, 2007.

*Primary Examiner*—Brij Shrivastav
*Assistant Examiner*—Tiffany A. Fetzner
(74) *Attorney, Agent, or Firm*—Cantor Colburn LLP

(57) ABSTRACT

A method and apparatus for obtaining a parameter of interest relating to a region proximate a nuclear magnetic resonance (NMR) logging tool suitable for subterranean well logging is disclosed. The nuclei of the region are subjected to a pulsed NMR technique and are productive of NMR logging data, the nuclei of the region characteristically having a longitudinal relaxation time $T_1$ distribution and an apparent transverse relaxation time $T_{2app}$ distribution. In response to the NMR logging data, an R distribution is defined as $R=T_1/T_{2app}$, the $T_{2app}$ and R distributions are processed as separate bins, along with the NMR logging data, according to a two-dimensional inversion model, and a signal intensity map of R versus $T_{2app}$ is provided that is representative of the parameter of interest relating to the region. In response to a high-intensity signal on the map being within a first range of $T_{2app}$ values and a first range of R values, the presence of a light hydrocarbon within the region is identified.

24 Claims, 8 Drawing Sheets
(3 of 8 Drawing Sheet(s) Filed in Color)

U.S. PATENT DOCUMENTS

| | | | |
|---|---|---|---|
| 2003/0107374 A1 | 6/2003 | Chen et al. | 324/303 |
| 2003/0201772 A1 | 10/2003 | Sigal et al. | 324/303 |
| 2003/0214286 A1* | 11/2003 | Heidler | 324/303 |
| 2003/0234648 A1 | 12/2003 | Ganesan | 324/303 |
| 2004/0032257 A1 | 2/2004 | Freedman | 324/303 |
| 2004/0140801 A1 | 7/2004 | Schoen | 324/303 |
| 2004/0169511 A1 | 9/2004 | Minh | 324/303 |
| 2004/0222791 A1 | 11/2004 | Chen | 324/303 |
| 2004/0251904 A1 | 12/2004 | Corver et al. | 324/321 |
| 2004/0251905 A1 | 12/2004 | Gozansky | 324/321 |
| 2005/0040822 A1* | 2/2005 | Heaton | 324/307 |
| 2005/0078001 A1 | 4/2005 | Abdelhadi | 340/854.9 |
| 2005/0104587 A1 | 5/2005 | Akkurt | 324/303 |
| 2005/0134266 A1 | 6/2005 | Kabasawa | 324/309 |
| 2005/0231198 A1 | 10/2005 | Beard et al. | 324/303 |
| 2005/0242807 A1 | 11/2005 | Freedman | 324/303 |
| 2005/0257610 A1 | 11/2005 | Gillen | 73/151.02 |
| 2005/0270023 A1 | 12/2005 | Freedman | 324/303 |
| 2006/0290350 A1* | 12/2006 | Hursan et al. | 324/303 |

* cited by examiner

METHOD AND APPARATUS FOR RESERVOIR FLUID CHARACTERIZATION IN NUCLEAR MAGNETIC RESONANCE LOGGING

BACKGROUND OF THE INVENTION

The present disclosure relates generally to a downhole nuclear magnetic resonance (NMR) apparatus, data processing, and interpretation methods for evaluating a characteristic of a region, and particularly for detecting and quantifying a gas-bearing earth formation in a subterranean region.

NMR well logging is a technique used to investigate subterranean regions that may contain water, oil and/or gas reserves. The nuclei of chemical elements have a characteristic angular momentum (spin) and a magnetic moment, and by detecting and analyzing the reaction of the nuclei to applied magnetic fields, the characteristics of specific nuclei may be deduced. In the presence of an externally applied static magnetic field ($B_0$), the nuclei spins become magnetized and align themselves parallel to the $B_0$ field. By applying a radio frequency (RF) pulse train of a specific frequency to the magnetized nuclei, a pulsed RF magnetic field ($B_1$) is generated that tips, or flips, the spins away from the direction of the $B_0$ field. If the RF frequency ($\omega$) substantially matches the condition for NMR ($\omega = \gamma B_0$), where $\gamma$ is the gyromagnetic ratio, then the first pulse (herein referred to as A pulse) reorients the magnetization to start precession and subsequent pulses (herein referred to as B pulses) generate spin-echo signals. A RF pulse sequence known as the CPMG (Carr-Purcell-Meiboom-Gill) sequence is typically used for well logging.

At the end of an A pulse, the spins are oriented transverse to the $B_0$ field and precess around the direction of the $B_0$ field at the Larmor frequency ($\omega_0 = \gamma B_0$), and the transverse magnetization dephases with a transverse relaxation time constant ($T_2$), also known as the spin-spin relaxation time. Repeated tipping and relaxation of the spins results in the NMR spin-echo signal, which may then be detected and analyzed for oil and/or gas field exploration.

Existing methods use dual wait-time logs and the $T_1$ contrast between gas and other formation fluids for gas detection and for gas saturation estimation. One such method is based on the assumption that water signals are fully polarized at both short and long wait time, TW, but gas signal is only partially polarized. So the difference between the two is contributed from gas only. However, if three phases coexist in the NMR detected sensitive volume, especially if slow relaxing water signal and light oil or oil-based mud filtrates are present in the formation, detection may be difficult or limited. Other methods for acquiring and processing multiple wait time data for $T_1$ estimation employ improved log quality data using a summation of echoes approach, which is more useful if all of the partially polarized signal is gas. However, the certainty of the signal is reduced for discerning gas using this technique for wells drilled with OBM (oil based mud), and the subsequent invasion of the OBMF (oil based mud filtrate) into the sensitive volume, or for formations containing large-pore water or light oil. Thus skilled human interpretation is required in order to use existing art techniques. Accordingly, there is a need in the art for a robust NMR detection and analysis method that overcomes these drawbacks.

BRIEF DESCRIPTION OF THE INVENTION

An embodiment includes a method for obtaining a parameter of interest relating to a region proximate a nuclear magnetic resonance (NMR) logging tool capable of generating a magnetic field B and a magnetic field gradient G, and pulse sequences suitable for subterranean well logging, the nuclei of the region being subjected to a pulsed NMR technique and being productive of NMR logging data, the nuclei of the region characteristically having a longitudinal relaxation time $T_1$ distribution and an apparent transverse relaxation time $T_{2app}$ distribution. In response to the NMR logging data, an R distribution as $R = T_1/T_{2app}$ is defined, the $T_{2app}$ and R distributions are processed as separate bins, along with the NMR logging data, according to a two-dimensional inversion model, and a signal intensity map of R versus $T_{2app}$ is provided that is representative of the parameter of interest relating to the region. In response to a high-intensity signal on the map being within a first range of $T_{2app}$ values equal to or greater than about a first $T_{2app}$ threshold value and equal to or less than about a second $T_{2app}$ threshold value, and a first range of R values equal to or greater than about a defined R threshold value, identifying the presence of a light hydrocarbon within the region.

Another embodiment of the invention includes a method for detecting and quantifying light hydrocarbons in a subterranean region proximate a nuclear magnetic resonance (NMR) logging tool capable of generating a magnetic field and field gradient G, and pulse sequences suitable for subterranean well logging, the nuclei of the region being subjected to a pulsed NMR technique and being productive of NMR logging data, the nuclei of the region characteristically having a longitudinal relaxation time $T_1$ distribution and an apparent transverse relaxation time $T_{2app}$ distribution. NMR logging data is acquired from the region, and in response to the acquired NMR logging data, an R distribution is defined as $R = T_1/T_{2app}$, the $T_{2app}$ and R distributions are processed as separate bins, along with the NMR echo data, according to a two-dimensional inversion model, and a signal intensity map of R versus $T_{2app}$ is provided that is characteristic of the nuclei in the region. In response to the location of a high-intensity signal on the map, a gas-bearing zone in the region is identified. A light hydrocarbon signal is represented on the map by a high-intensity signal occurring in a first range of R values and a first range of $T_{2app}$ values, and a liquid phase signal is represented on the map by a high-intensity signal occurring in a second range of R values and a second range of $T_{2app}$ values.

A further embodiment of the invention includes a nuclear magnetic resonance (NMR) well logging apparatus for detecting and quantifying light hydrocarbons in a subterranean region. The apparatus includes a field gradient generator capable of applying a static magnetic field gradient to a subterranean region, a signal generator capable of applying sequences of magnetic pulses to the region, a signal receiver capable of receiving information from nuclei in the region responsive to the magnetic field gradient and the magnetic pulses, a processing circuit configured to process the received information, and a storage medium, readable by the processing circuit, storing instructions for execution by the processing circuit for practicing method embodiments of the invention. In an embodiment, NMR logging data relating to the region is received, and in response to the received NMR logging data, an R distribution is defined as $R = T_1/T_{2app}$, the $T_{2app}$ and R distributions are processed as separate bins, along with the NMR logging data, according to a two-dimensional inversion model, and a signal intensity map of R versus $T_{2app}$ is generated that is characteristic of the nuclei in the region. The presence of a gas-bearing zone in the region is signified in response to a high-intensity signal on the map being within a first range of $T_{2app}$ values equal to or greater than about a first $T_{2app}$ threshold value and equal to or less than about a second $T_{2app}$ threshold value, and a first range of R values equal to or greater than about a defined R threshold value. The presence of a liquid phase substance in the region is signified in response to a high-intensity signal on the map having an R value equal to or greater than but substantially close to 1 for any value of $T_{2app}$.

BRIEF DESCRIPTION OF THE DRAWINGS

The patent or application file contains at least one drawing executed in color. Copies of this patent or patent application publication with color drawings will be provided by the Office upon receipt and payment of the necessary fee.

Referring to the exemplary drawings wherein like elements are numbered alike in the accompanying Figures.

DETAILED DESCRIPTION OF THE INVENTION

Figure 1:
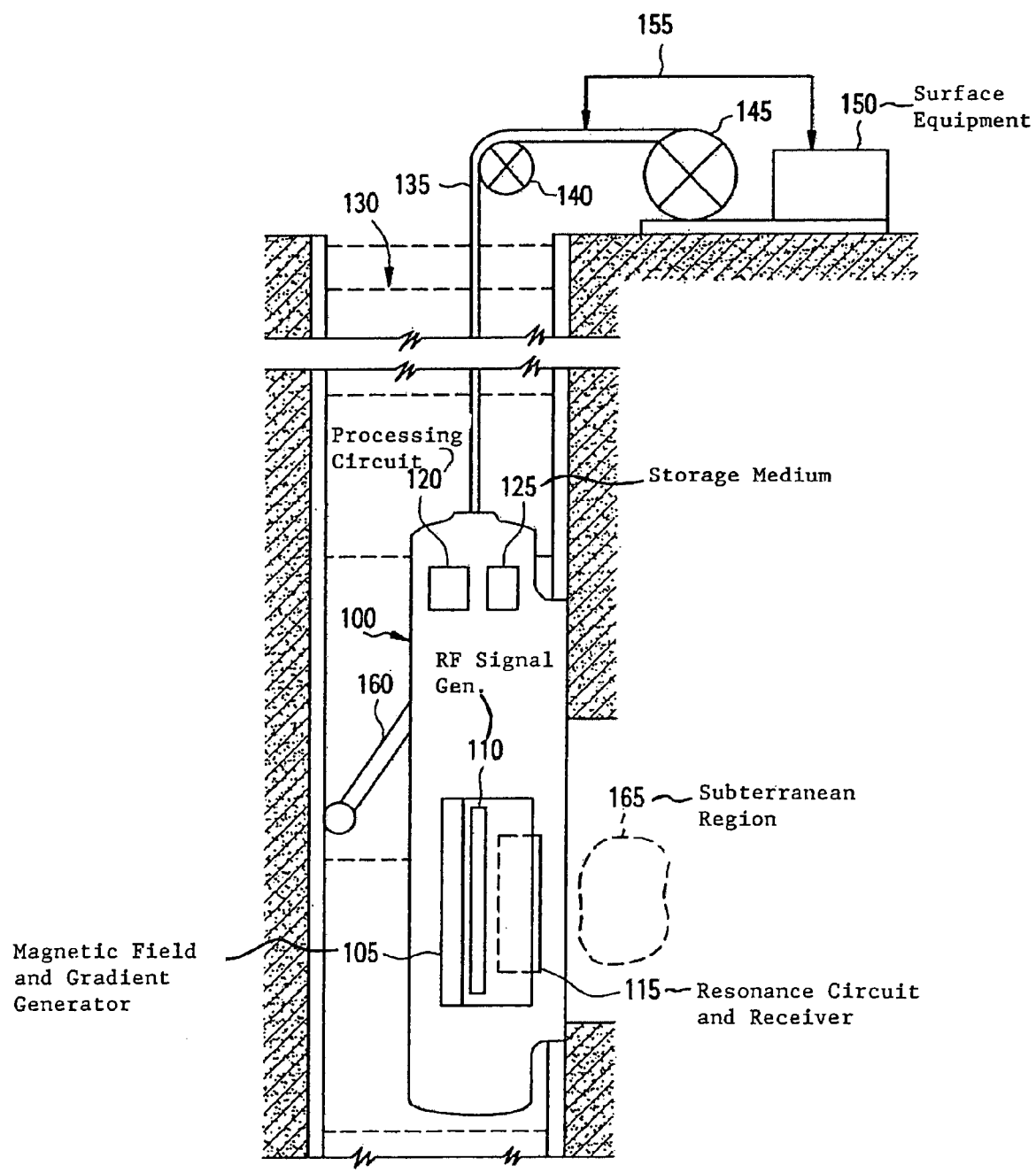
FIG. 1 depicts an exemplary well logging apparatus for practicing an embodiment of the invention.

Embodiments of the invention provide a nuclear magnetic resonance (NMR) wellbore logging method and apparatus for applying a sequence of magnetic field pulses to a subterranean region so as to magnetically excite the region in such a manner that enables a data processing method to identify and quantify light hydrocarbons from the NMR logging data. A two-dimensional inversion method is used to obtain images of the ratio of $T_1/T_{2app}$ vs. $T_{2app}$ from NMR logs acquired using multiple wait times (TW), which is represented by a signal intensity map. Embodiments disclosed herein, however, are not limited to the use of multiple wait times. The technique is particularly useful and robust for detecting and quantifying light hydrocarbons such as gas and retrograde condensates. In another embodiment, it can also be used to detect the existence of large vugs in carbonate formations.

An embodiment of the invention is particularly useful in situations where a large diffusion contrast, and consequently a large $T_1/T_{2app}$ contrast, exists. As such, embodiments of the invention are useful for discerning gas from liquids, such as oil and water. Instead of the existing methodologies of inverting one-dimensional $T_1$ and $T_2$ relaxation times separately, or inverting two-dimensional $T_1$ and $T_2$ relaxation times jointly, in an exemplary embodiment, it will be appreciated that a direct inversion of $T_1/T_{2app}$ vs. $T_{2app}$ offers significant advantages.

First, the high $T_1/T_{2app}$ contrasts between gas and liquid provides a distinctive signature on a $T_1/T_{2app}$ vs. $T_{2app}$ image (map) that facilitates robust data interpretation. Second, by selecting the frequencies (and, thus, the magnetic field gradients) and/or inter-echo time (TE), the gas $T_{2app}$ is constrained to a narrow range, for example, from about 40 milliseconds (msec) to about 150 msec. Thus, the gas signal location on the $T_1/T_{2app}$ vs. $T_{2app}$ image is always narrowly defined, which substantially simplifies data interpretation. Third, physical constraints, such as $T_1/T_{2app}$ may be more readily applied to reduce some noise-induced uncertainties. Furthermore, it is often difficult to construct the $T_1/T_{2app}$ ratio from $T_1$ and $T_2$ based on predetermined times (that is, bins) as the inversion artifacts and noise effects make bin-by-bin computations nearly impossible. Thus, bin-to-bin ratios work at most only for gas wells where a significant amount of gas signal is apparent. Advantageously, the techniques disclosed herein work even when gas-saturation levels are relatively small. In addition, exemplary embodiments employing the inversion processing method disclosed herein work well even when the echo data are relatively noisy (in a salt-saturated mud well for example). Further embodiments of the invention enable the $T_1$ spectra to be reconstructed from the recovered $T_1/T_{2app}$ and the corresponding $T_{2app}$ spectra.

Hereinafter, the following terminology will be employed:

D Diffusivity of fluid.

G Magnetic field gradient. Generally, G is the NMR tool's field gradient. For typical well logging tools, such as MREX$^{SM}$ tool available from Baker Hughes Incorporated, G is frequency dependent. However, a frequency dependent G is not a requirement. In an embodiment, the NMR logging tool has a magnetic field gradient G of about 20 or 30 Gauss/cm.

$T_1$ Longitudinal relaxation time.

$T_2$ Transverse relaxation time.

$T_{2app}$ Apparent $T_2$, where $1/T_{2,app}=1/T_{2,int}+1/T_{2,diff}$.

$T_{2bulk}$ Bulk $T_2$, which is the $T_2$ relaxation time measured in the bulk state. For non-wetting fluids, $1/T_{2bulk} \approx 1/T_{2,int}$.

$T_{2diff}$ Additional $T_2$ decay due to diffusion in a gradient field, where $1/T_{2diff}=(\gamma \cdot G \cdot TE)^2 D/12$.

$T_{2int}$ Intrinsic $T_2$, $1/T_{2,int}=1/T_{2bulk}+1/T_{2surf}$.

$T_{2surf}$ Surface $T_2$, which is the surface contribution of the $T_2$ relaxation time.

TE Interecho time, which is the time between two adjacent echoes. In an embodiment, the NMR logging tool has an echo time spacing TE of about 1 millisecond.

TW Wait time, which is the time between the last data acquired in the previous data acquisition event and the first excitation pulse of the current data acquisition event of the same frequency.

γ Gyromagnetic ratio.

FIG. 1 is an exemplary embodiment of a nuclear magnetic resonance (NMR) well logging apparatus 100 suitable for detecting and quantifying light hydrocarbons in a subterranean region. In an exemplary embodiment, apparatus 100 includes a magnetic field and field gradient generator 105, such as a permanent magnet for example, a rf signal generator 110, a resonance circuit and receiver 115, a processing circuit 120, and a storage medium 125. In an exemplary application, logging apparatus 100 is suspended in a borehole 130 via a cable 135, a pulley 140, a drivewheel 145, and surface equipment 150, which controls the lowering and raising action of cable 135 as represented by control line 155. Apparatus 100 may be pressed against one side of borehole 130 via a control arm 160. Field gradient generator 105 is capable of applying a static magnetic field gradient G to the subterranean region, generally represented at 165. Signal generator 110 is capable of applying a sequence of magnetic pulses to region 165, and signal receiver 115 is capable of receiving information, and specifically nuclear magnetic resonance information, from the nuclei of region 165 in response to the magnetic field gradient from field gradient generator 105 and the magnetic pulses from signal generator 110. The nuclei of the region, being subjected to a pulsed NMR technique, are productive of NMR echo data, and characteristically have a longitudinal relaxation time $T_1$ distribution and an apparent transverse relaxation time $T_{2app}$ distribution. In an embodiment, the pulses from signal generator 110 and the information received at signal receiver 115 are controlled and processed by processing circuit 120. Storage medium 125, readable by processing circuit 120, stores instructions for execution by processing circuit 120 for performing method embodiments of the invention, which will now be discussed in more detail.

The NMR response (M) measured with a CPMG acquisition sequence may be expressed in terms of $T_1$ and $T_{2app}$ as $$M = \int_0^\infty \int_0^\infty f(T_{2app}, T_1)\left(1 - e^{-\frac{TW}{T_1}}\right)e^{-\frac{t}{T_{2app}}} dT_{2app} dT_1 \quad (1)$$

where the double integral is integrated over all time $T_{2app}$ and $T_1$, and where t represents the time at which the current echo is acquired which equates the time between adjacent echoes (TE) multiplied by the echo index (discussed below).

In Equation-1, all fluid relaxation properties are embedded in the two-dimensional relaxation distribution function $f(T_{2app}, T_1)$. From the definition of $T_1$ and $T_{2app}$, it follows that $T_1 \geq T_{2app}$. In exemplary embodiments of the invention, this constraint is introduced with the variable R, where $R = T_1/T_{2app}$, thereby enabling the response function of Equation-1 to be reformulated as $$M = \int_1^\infty \int_0^\infty g(T_{2app}, R)\left(1 - e^{-\frac{TW}{R \cdot T_{2app}}}\right)e^{-\frac{t}{T_{2app}}} dT_{2app} dR \quad (2)$$

where $g(T_{2app}, R)$ defines a signal intensity function that is solved for using a numerical two-dimensional inversion method that will be discussed in more detail below.

Figure 3:
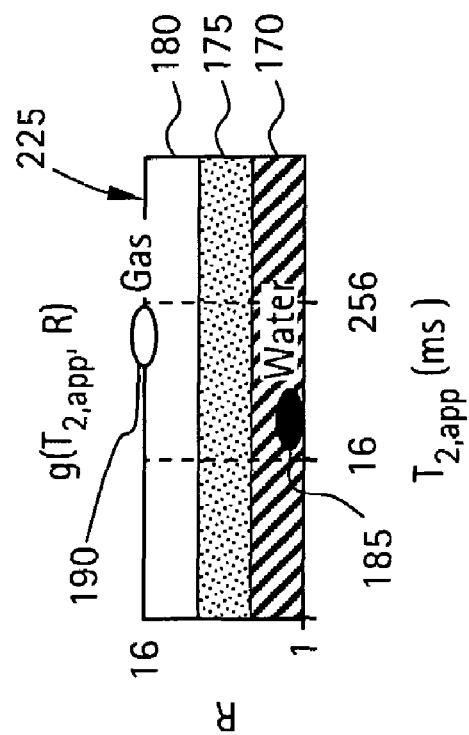
FIGS. 2 and 3 depict graphical representations illustrating the relationship between density functions $f(T_{2app}, T_1)$ and $g(T_{2app}, R)$ in accordance with an embodiment of the invention.
Figure 2:
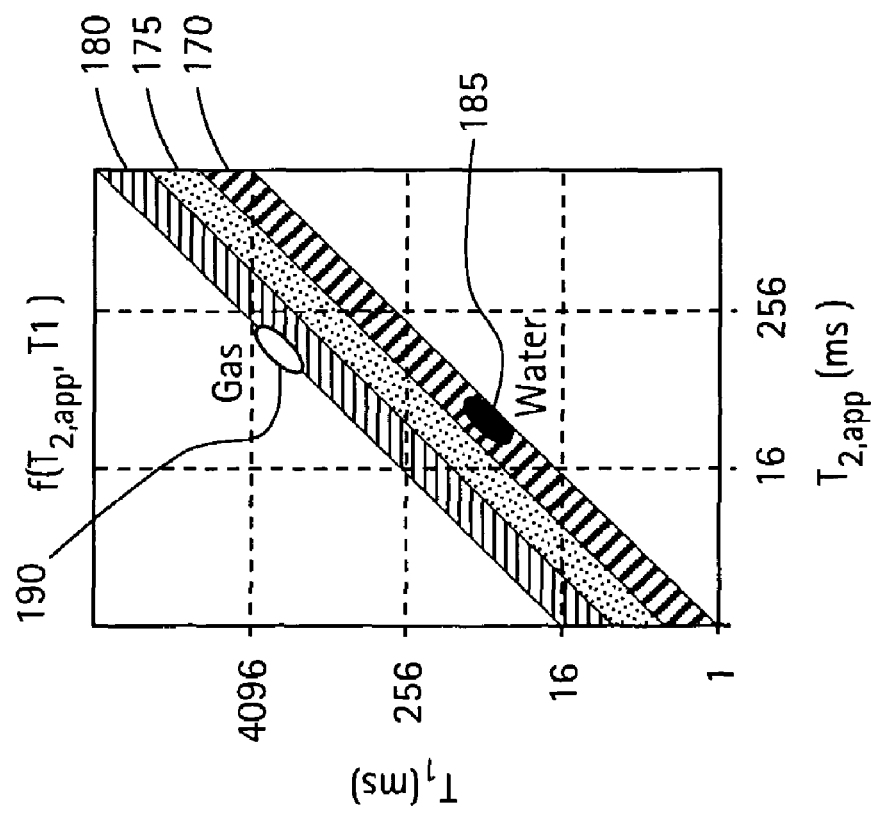

Graphical representations illustrating the relationship between density functions $f(T_{2app}, T_1)$ and $g(T_{2app}, R)$ are depicted in FIGS. 2 and 3, where rectangular model domains are defined such that they include most common fluid properties occurring in well logging applications with exemplary state-of-art NMR logging tools. Conversion between the two models may be seen by comparing the three equivalent fluid property ranges 170, 175, 180 that are marked with similar shading patterns. In the exemplary embodiment depicted by FIGS. 2 and 3, a gas containing water-wet porous formation may be depicted where the water part is represented by $T_1(w)=30$ msec, $T_{2diff}(w)=300$ msec, and the gas part is represented by $T_1(g)=3000$ msec, $T_{2diff}(g)=200$ msec. Applying the terminology relationships presented earlier, the $T_{2app}$ values for the water and gas parts may be calculated as $T_{2app}(w)=(300*30)/(300+30)=27.3$ msec and $T_{2app}(g)=(200*3000)/(200+3000)=187.5$ msec. Applying the definition for $R=T_1/T_{2app}$, yields $R(w)=1.1$ and $R(g)=16$. The positions of these typical fluids on the $T_1$ vs. $T_{2app}$ map and the R vs. $T_{2app}$ map are illustrated by a filled oval 185 for water, and an empty oval 190 for gas, in FIGS. 2 and 3. As can be seen, the R vs. $T_{2app}$ representation requires much fewer model parameters in the y-axis dimension to span the same fluid range, effectively addressing resolution problems due to the limited number of different TW values in a typical downhole NMR measurement.

Equation-2 may be represented in numerical form as $$M(t_k, TW_l, G) = \sum_i \sum_j m_{i,j}(1 - \exp(-TW_l/(T_{2app,j} \cdot R_j)))\exp(-t_k/T_{2app,i}) \quad (3)$$

where the ratio $R=T_1/T_{2app}$ is expanded to be $$R = \frac{T_1}{T_{2,app}} \quad (4)$$

$$= \frac{kT_{2,int}}{T_{2,app}}$$

$$= \frac{kT_{2,int}}{T_{2,int}} + \frac{T_{2,int}}{T_{2,diff}}$$

$$= k + \frac{(\gamma GTE)^2 D \cdot T_{2,int}}{12}$$

$$\approx 1 + \frac{(\gamma GTE)^2 D \cdot T_{2,int}}{12}$$

In Equation-4, the variable k is defined as $k=T_1/T_{2int}$, which is approximately equal to 1 for fluids of interest in wellbore logging, thereby resulting in R being dependent on the diffusivity D of the fluid in region 165. Since $D_{gas} >> \max(D_{oil}, D_{water})$, the ratio $R=T_1/T_{2app}$ is close to 1 for a liquid-phase signal, but is much greater than 1 for a gas-phase signal. As a result of this distinctive feature between gas and liquids, embodiments of the invention are particularly useful for gas identification.

In Equation-3, the "i" indice refers to i-th $T_{2app}$ relaxation time ($T_{2appi}$), the "j" indice refers to the j-th $T_1$ ($R*T_{2app}$) relaxation time ($R_j*T_{2appj}$), the "k" indice (echo index) refers to the k-th echo which is acquired at ($t=k*TE$) or ($t_k$), and the "l" indice refers to the l-th wait time ($TW_l$). The matrix $m_{ij}$ refers to the solution map for the signal intensity function $g(T_{2app}, R)$.

As can be seen from Equation-3, embodiments of the invention may employ multiple wait time (TW) data. However, alternative embodiments may employ single TW data.

Figure 4A:
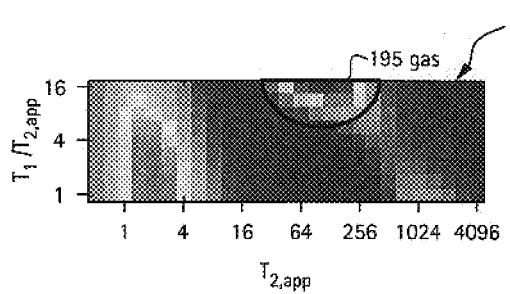
FIGS. 4A and 4B depict graphical representations of exemplary solutions of signal intensity function $g(T_{2app}, R)$ in accordance with embodiments of the invention.
Figure 4B:
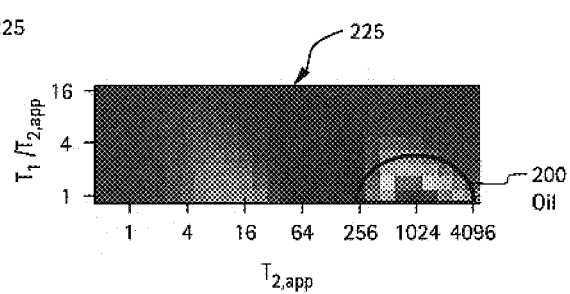

The solution to Equation-3, which yields values for matrix $m_{ij}$, involves a two-dimensional (2D) inversion processing method that yields a map 225 of $T_1/T_{2app}$ vs. $T_{2app}$ distributions, as illustrated by FIGS. 3, 4A and 4B. In contrast, the traditional one-dimensional (1D) inversion processing method calculates the apparent $T_2$ only. Like the requirement of setting $T_{2int}$ bins and diffusivity $D_j$ bins in the 1D method, embodiments of the herein disclosed 2D method require a predetermination of both the $T_{2appi}$ bins and the ratio $(R=T_1/T_{2app})_j$ bins, respectively, which is represented by the indices of Equation-3.

By treating the $T_1/T_{2app}$ and $T_{2app}$ parameters independently, these unknowns become generic parameters (bins), instead of linking them to individual fluid types. Consequently, fluid-typing interpretation of the instant invention is carried out in the parameter domain rather than at the inversion stage. As such, embodiments of the invention are different from forward-modeling based inversion techniques, such as SIMET (simultaneous inversion of multiple echo trains) for example.

Once the distributions of $R=T_1/T_{2app}$ and $T_{2app}$ are determined, the distributions of R and $T_{2app}$ may be used to generate a $T_1$ distribution by applying the following matrix equation, where matrix parameters are depicted in boldface, $$T_1 = RT_{2app}, \quad (5)$$

and the power density $p_j$ of the $T_1$ distribution may be reconstructed from the $T_{2appi}$ distribution using $m_{ij}(T_{2appj})$ according to the following equation $$p_j(T_1) = \sum_i m_{i,j}(T_{2app_j}). \quad (6)$$

Reformulating Equation-3 into a matrix equation yields $$d = A*m, \quad (7)$$

where $$d_i = M(t, TW)_i = M(t_{w(n)}, TW_n)_i, \quad (8)$$

and where $d_i$ includes all echoes that may be acquired from multiple echo trains, that is, $$i = \sum_{l=1}^{n-1} W(l) + w(n), \quad (9)$$

where $W(l)$ is the length of the l-th echo train and $w(n)$ is the w-th element of the n-th echo train. For a given i-th $T_{2app}$ relaxation time, the j-th element of the $m_{ij}$ solution map becomes, $$m_j = g(T_{2app}, R)_j = g(T_{2app,u}, R_v)_j, \quad (10)$$

$$\text{where } j = \sum_{l=1}^{v-1} U(l) + u(v),$$

and where $U(l)$ is the length of the $T_{2app}$ vector corresponding to the l-th R, and $u(v)$ is the u-th $T_{2app}$ value of the v-th R. To ensure consistency of indices between Equation-3 and Equation-7, the exponential terms of Equation-3 as applied to Equation-7 may be written as $$A_{ij} = \left(1 - e^{-TW_{i(w,n)}/(R \cdot T_{2app})_{j(u,v)}}\right) e^{-t_{i(w,n)}/(T_{2app})_{j(u,v)}}. \quad (11)$$

From the foregoing, it will be appreciated that Equation-8 is representative of the observed NMR echo data $M_i$, which constitutes the left side of Equation-7, and $m_j$ represents the unknown intensities of $g(T2app, R)_j$, which is on the right side of Equation-7. Accordingly, and to solve for $m_j$, one must multiply both sides of Equation-7 by the inverse of the two-dimensional matrix $A_{ij}$ from Equation-11. The solution of which results in the j-th value of signal intensity map $m_{ij}$ for each i-th $T_{2app}$.

Due to the existence of noise in NMR logging data and the ill-conditioned nature of matrix A, the solution to Equation-7 can be challenging. To assist in a suitable solution for matrix m, which reduces random noise effects and provides a smoother curve fit of model to data, a regularized non-negative least square formulation is applied to the inversion model according to the following equation $$\|Am-d\|_2^2 + \alpha\|W_m m\|_2^2 = \min \text{ subject to } m \geq 0. \quad (12)$$

In Equation-12, the notation "$\|\ \|$" stands for the Euclidean norm of its vector argument (or the maximum singular value of the matrix argument). The first term $\|Am-d\|$ of Equation-12 comes from Equation-7, and represents the least square portion that serves to minimize the misfit by fitting the model matrix m to the data matrix d. The second term $\alpha\|W_m m\|$ of Equation-12 is a regularization term that serves to penalize the solution by fitting the model matrix m to the data matrix d to a minimum "min" level that is higher than the model and data alone, thereby making the solution more stable and smoother.

The regularization parameter $\alpha$ is estimated from the results of a relatively inexpensive preliminary non-constrained inversion, such that it balances the contributions of the misfit (first) and stabilizer (second) terms. It produces similar $\alpha$ estimates to the well known L-curve or S-curve methods at a lesser cost. Matrix $W_m$ embodies additional information about the desired solution, which is discussed in more detail below. The method of regularization and Least Squares minimization is not limited to a particular algorithm, and employs known techniques.

To single out a useful and stable solution, the stabilizer term in Equation-12 is defined such that $W_m$ is nonsingular. In an exemplary embodiment, it is either the identity matrix or an $n^{th}$ derivative operator, which forces the solution to be small and/or smooth. However, in NMR logging applications it is often desirable to strive for solutions with a high spectral resolution from noisy data. Such sharp features may be achieved by using focusing stabilizers, where the basic idea is described as follows. After obtaining an initial solution, typically by a smooth stabilizer, very small elements $m_s < \epsilon \cdot \max(m)$ are excluded. Then, a second minimization process is run with $W_m(k,k) = \max(m)/m_k$. A small $m_k$ results in a large weight in the stabilizer of the second step, forcing that particular element to be even smaller. The procedure is repeated until no further elements are excluded, that is, only those elements with significant contribution remain. In applying this process, care should be exercised to avoid over-focusing, where only one or a few elements remain. This may be accomplished by defining different termination criteria, or by applying additional side constraints, which will now be described.

Embodiments described herein employing the 2D inversion method having $T_{2app}$ as one of the dimensions has a distinctive advantage over those methods involving $T_{2int}$ because of the straightforward connection to the standard 1D $T_{2app}$ spectra. Also by selectively controlling the data acquisition parameters (such as frequency and TE for example), the $T_{2app}$ for gas is predictably controlled in the middle of the commonly occurring $T_{2app}$ range. Water in this $T_{2app}$ range generally has only a small diffusion effect. Theoretically, the summation of the $g(T_{2app}, R)$ along R matches the $T_{2app}$ spectra derived from a single fully polarized echo train. Therefore, a constraint may be constructed that requires the sum of the corresponding 2D parameters to be the same as the readily available $T_{2app}$ distribution. That is, the sum of the two-dimensional intensity map 225 is constrained in the vertical direction with respect to the $T_{2app}$ axis so that it is the same as a corresponding standard one-dimensional $T_{2app}$ distribution. This constraint not only serves as a useful side constraint in the focusing inversion, but it also makes the 1D and 2D inversion method results consistent. This side constraint methodology is referred to as a 1D constraint.

An exemplary result from an embodiment of the 2D inversion method is a set of 2D images similar to those depicted in FIGS. 4A and 4B, which may be presented in color, shades of gray, high and low density speckling, varied cross-hatching, or any other visually defining scheme. In the exemplary embodiments depicted by FIGS. 4A and 4B, the signal intensities from the solution of $g(T_{2app}, R)$, alternatively referred to as the solution map 225, are each plotted and illustrated with respect to a color-coded image intensity scale, with red representing a high signal intensity and blue representing a low signal intensity. Here, FIG. 4A illustrates a gas signal 195, while FIG. 4B illustrates an oil signal 200. Because gas has a higher R value than either oil or water, the gas signal, if any, appears at the top middle of the 2D plot (see FIG. 4A). If the interval of interest has a liquid signal only, the bright spot (high signal intensity) is close to the bottom of the 2D plot (see FIG. 4B). The horizontal location (along the $T_{2app}$ axis) of the gas signal on the 2D image depends on gas properties (dry or wet for example), environment (temperature and pressure for example), and the gas constituents (methane or ethane for example), as well as experimental conditions (frequency and TE for example). For data acquired with the known standard PoroPerm+Gas sequence acquisition, the gas signal is usually shown in the $T_{2app}$ range between 64 msec to 256 msec. A water signal location depends on pore structures, and an oil signal location depends on viscosity.

In addition to the R plot, a reconstructed $T_1$ log may be plotted along with $T_{2app}$ log. The following Table-1 provides guidance on how to identify a gas signal from a comparison between the $T_1$ and $T_{2app}$ logs.

TABLE 1

| | Signal shown | | |
|---|---|---|---|
| | On $T_1$ log | On $T_{2app}$ log | Interpretation |
| Center of 512-8192 msec→ | Yes | No | gas |
| and 64-512 msec → | No or weaker | Yes or strong | |
| Center of 512-8192 msec | Yes | Yes | No gas, or gas mixed with liquid, check 2D to confirm |
| Center of 512-8192 msec | No | No | No gas. (if seen this in a gas zone, flush is too severe) |

Figure 5:
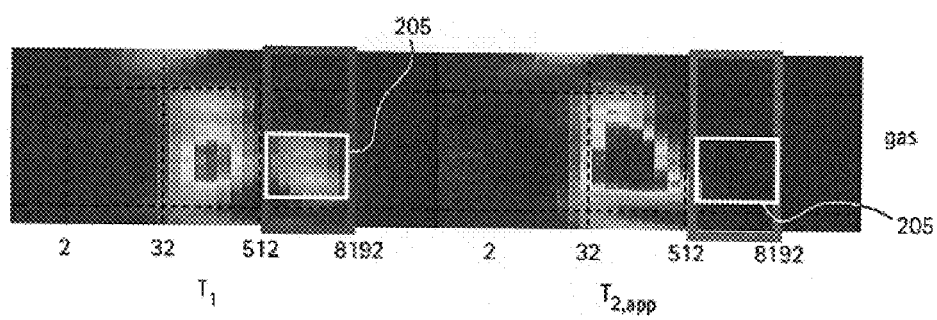
FIG. 5 depicts a graphical representation of a likely observance on a $T_1$ and $T_{2app}$ log comparison for a gas zone, where the presence of a gas signal requires a comparison of the two logs.

FIG. 5 illustrates a likely observance on a $T_1$ and $T_{2app}$ log comparison for a gas zone, where the presence of a gas signal 205 requires a comparison of the two logs. As with FIGS. 4A and 4B, the illustration of FIG. 5 may be presented in color, shades of gray, or any other visually defining scheme.

In addition to the qualitative observation of the one-dimensional $T_1$ and $T_{2app}$ logs, the clear separation of the gas and liquid phases in the two-dimensional representation and/or in the $T_1$ and $T_{2app}$ logs, may be used to quantify gas and liquid filling pore volumes and the corresponding saturations.

The apparent volume of gas may be obtained by summing up intensities in the domain defined as R≧Rc, where Rc is defined as a cutoff threshold value of R. The cutoff value Rc is defined such that high-intensity signals having a value of R equal to or greater than Rc are categorized as light hydrocarbon signals and high-intensity signals having a value of R less than Rc are categorized as liquid phase signals. The apparent volume of gas ($V_T$) in the region 165 is determined by summing up the light hydrocarbon signal intensities in the map 225 domain defined by R equal to or greater than Rc. The actual gas volume ($V_g$) is obtained by applying a hydrogen index correction ($HI_g$) to the apparent gas volume ($V_T$), thereby defining an HI corrected pore volume, according to the following equation:

$$HI_g = V_g/V_T. \qquad (13)$$

The liquid pore volume in the region 165 is determined by summing of intensities in the map 225 defined by R<Rc, where a hydrogen index correction may be applied if necessary. The total porosity in the region 165 is obtained by summing the actual gas (HI corrected) pore volume with the liquid pore volume. The gas saturation, being a function of the HI corrected pore volume and the total porosity, is determined by taking the ratio of the actual gas volume over the total pore volume.

Figure 6:
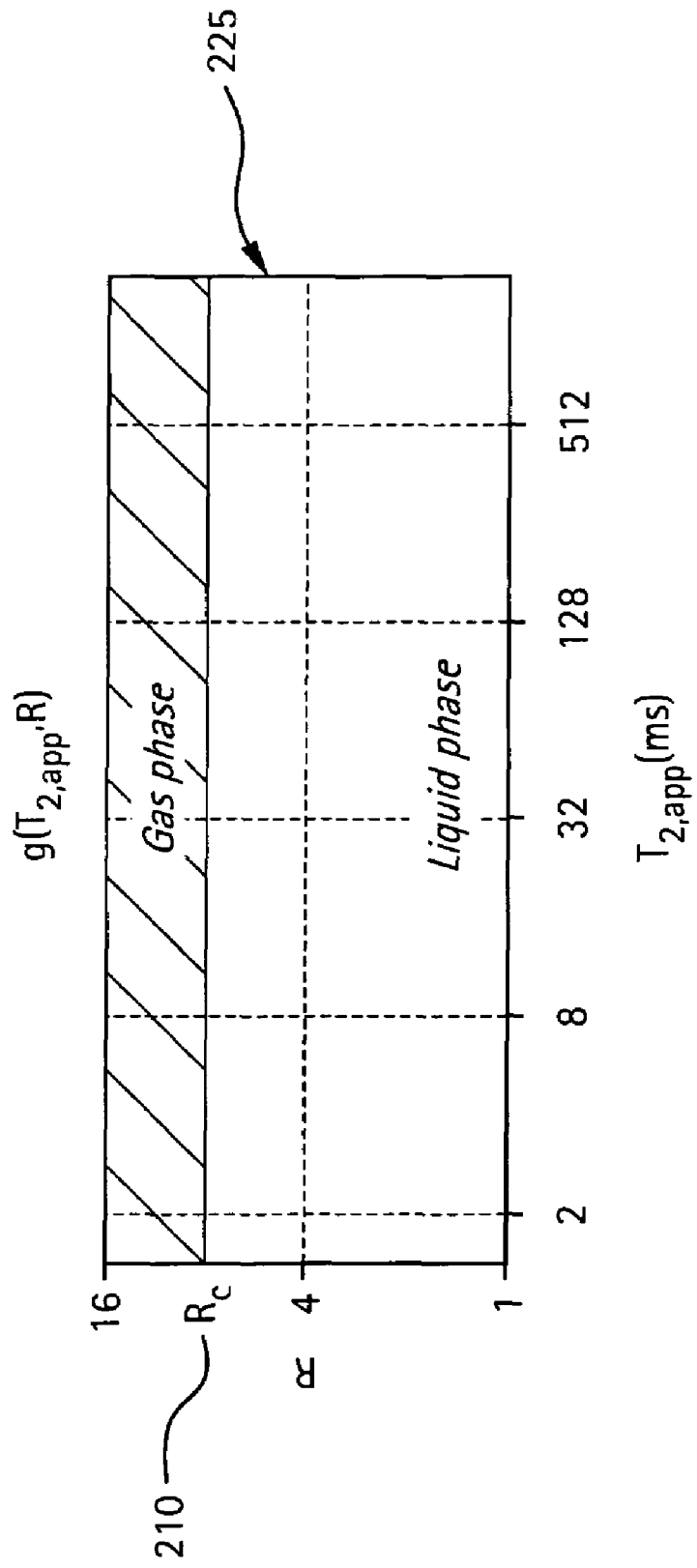
FIG. 6 depicts a graphical representation of cutoff threshold value Rc as applied to a two-dimensional signal intensity image map $g(T_{2app}, R)$ in accordance with an embodiment of the invention.

FIG. 6 illustrates the application of the cutoff threshold value Rc 210 to the 2D signal intensity image map 225 of $g(T_{2app}, R)$. The boundaries of the parameter domain and the value of Rc are calculated by taking into consideration borehole temperature, borehole pressure, gas compositions in the area, acquisition parameters G and TE, and measurement noise. The $T_{2app}$ bounds are determined by TE and the field gradient value G used for acquiring the echo trains, and the fluid property that may be affected by temperature and pressure. For example, a typical $T_{2app}$ for MR Explorer$^{SM}$ (MR Explorer$^{SM}$ is a magnetic resonance openhole wireline logging tool available from Baker Hughes Incorporated) has a data range between 0.5 and 2048 msec. The discretization density used for volume modeling is typically chosen to be the square-root of 2, but is not limited to this number.

In the calculation of the upper bound in R, it is desirable to constrain the number of unknowns in the R direction so that they do not significantly exceed the number of different wait times (TW). However, it is desirable for the upper bound in R to significantly exceed the highest expected fluid R value so that the gas signal is appreciably separated from the fluid signals. Since $T_1 \geq T_{2app}$, the minimum value of R is always 1.

As an example, in a typical PoroPerm+Gas acquisition with 6 different wait times (TW), it is desirable for the number of different R values not to be greater than 9. Using the same bin increments as for $T_{2app}$, a value of Rmax=16 is obtained, which leaves enough room to separate the gas signal from most liquid phase signals, which have an R value that is almost always below 4 to 6, in the case of TE≦0.6 msec. In an embodiment, an Rc of 10 is selected, such that signal intensities having a value of R≧10 is representative of a gas-phase substance, and signal intensities having a value of R<10 is representative of a liquid-phase substance, which is illustrated in FIG. 6.

Figure 7:
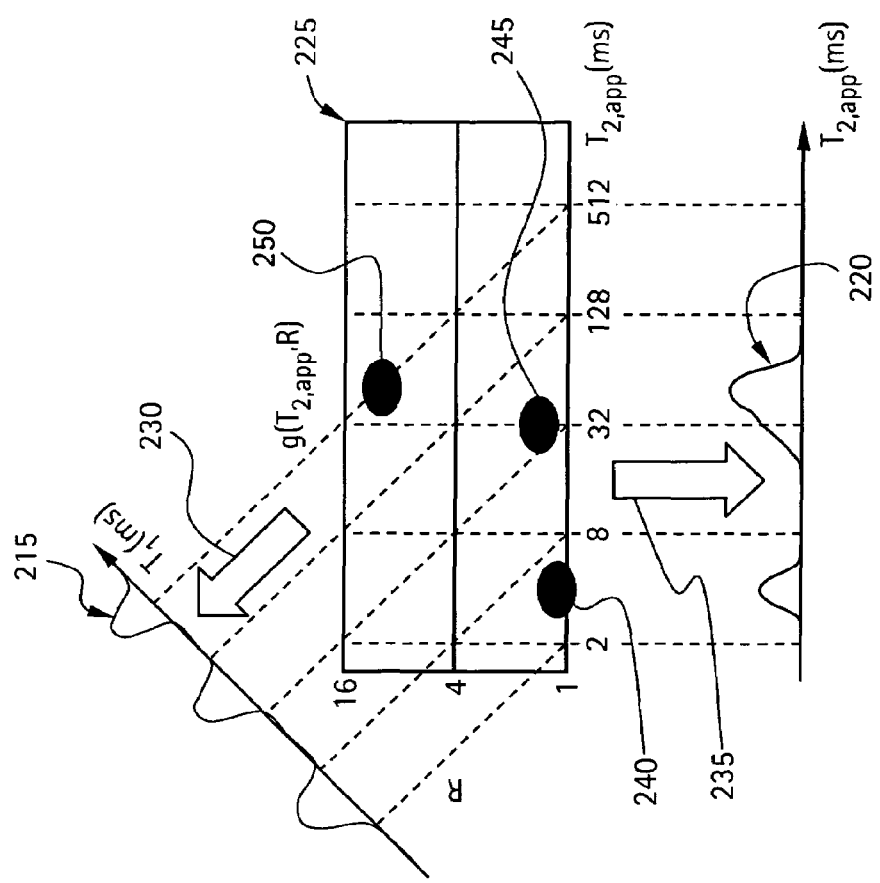
FIG. 7 depicts a graphical representation of reconstructed one-dimensional $T_1$ and $T_{2app}$ distributions in accordance with an embodiment of the invention.

Referring now to FIG. 7, the one-dimensional $T_1$ and $T_{2app}$ distributions 215, 220 may be obtained from the 2D intensity plot 225 by summing up the 2-dimensional intensity plot 225 along the directions of the arrows 230, 235 pointing towards the 1-dimensional plots 215, 220. For example, the one-dimensional $T_{2app}$ distribution 220 may be determined by summing up the two-dimensional intensity map 225 in a vertical manner (arrow 235) with respect to the $T_{2app}$ axis, and the one-dimensional $T_1$ distribution 215 may be determined by summing up the two-dimensional intensity map 225 from the $T_{2app}$ axis in a diagonal manner (arrow 230) toward the R axis. In FIG. 7, high-intensity signals are depicted by shaded ovals 240, 245 and 250. The one-dimensional representations may be used to obtain standard NMR deliverables, such as MCBW (MR clay bound water), MBVI (MR bulk volume irreducible), MBVM (MREX bulk volume movable), MPHS (MR total porosity), MPHE (MR effective porosity), and MPRM (MR permeability), for example. Also, the $T_{2app}$ and $T_1$ distributions may be reconstructed into logs in response to the distributions having been determined on a depth by depth basis.

In an embodiment and from the reconstructed one-dimensional $T_{2app}$ and $T_1$ distributions, the presence of a gas-bearing zone in region 165 may be determined in response to a high-intensity signal having a $T_{2app}$ relaxation time less than about 512 msec, and a $T_1$ relaxation time equal to or greater than about 512 msec and equal to or less than about 8192 msec.

The $T_1$ processing is insensitive to the very fast relaxing fluid components such as CBW and some BVI because a limited number of short TWs is applied. However, $T_{2app}$ always yields more accurate CBW and BVI information. Thus, it is recommended to use the $T_{2app}$ based rather than the $T_1$ based CBW and BVI.

Figure 8:
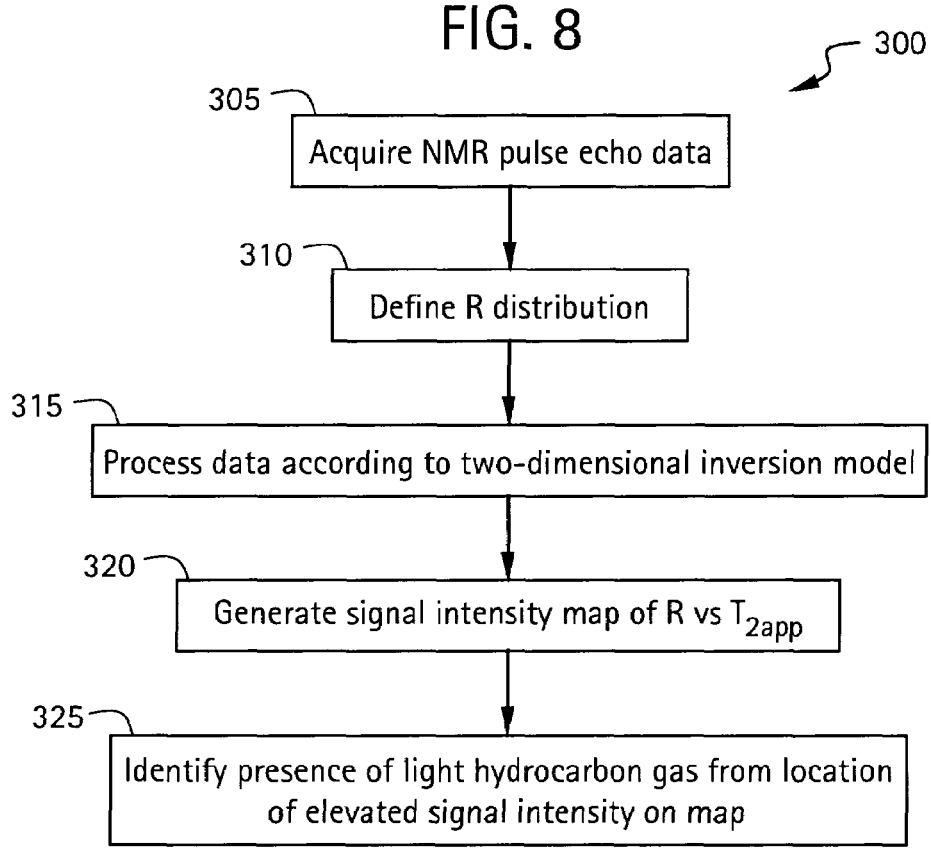
FIG. 8 depicts a flow diagram of a method in accordance with an embodiment of the invention.

In accordance with the foregoing discussion, it will be appreciated that embodiments of the invention include a NMR well logging tool 100 capable of generating a magnetic field gradient G, a pulse echo time spacing TE, and a pulse wait time TW suitable for subterranean well logging, and capable of practicing the method 300 depicted in the flow diagram of FIG. 8.

With reference to FIG. 8 and in accordance with an embodiment of the invention, NMR echo data (also herein referred to as NMR logging data in relation to a log) is acquired 305, an R distribution is defined 310 according to Equation-4, and a signal intensity map 225 is generated 320 by processing 315 the $T_{2app}$ and R distributions as separate bins along with the NMR echo data in accordance with Equations-3 and 7, where the inverse of the two-dimensional matrix A from Equation-11 is applied to solve for matrix m. The resultant signal intensity map 225 (depicted in illustrative form by FIGS. 3, 6 and 7, and in numerical solution form by FIGS. 4A and 4B) is generally representative of a parameter of interest relating to the region 165, and in an embodiment is specifically representative of the presence of light hydrocarbon within the region 165, as depicted by FIG. 4A. According to the teaching disclosed herein regarding the R vs. $T_{2app}$ characteristics of gas-phase and liquid-phase substances in region 165, it is possible to identify 325 the presence of light hydrocarbon from the location of a high-intensity signal on the map 225. In an exemplary embodiment, and with Reference to FIG. 4A, a gas signal, signifying a gas-bearing zone within region 165, occurs on map 225 within a first range of $T_{2app}$ values equal to or greater than about 16 msec and equal to or less than about 256 msec, and a first range of R values equal to or greater than about 10. In another exemplary embodiment, the light hydrocarbon signal represented on the map 225 has a value of $T_{2app}$ equal to or greater than about 64 msec. In a further exemplary embodiment, and with reference to FIG. 4B, a liquid-phase signal, signifying a liquid-phase substance within region 165, occurs on map 225 at an R value equal to about 1 for any value of $T_{2app}$. From different map signatures, a gas-bearing zone may be identified as containing retrograde condensates or dry gases.

Figure 9:
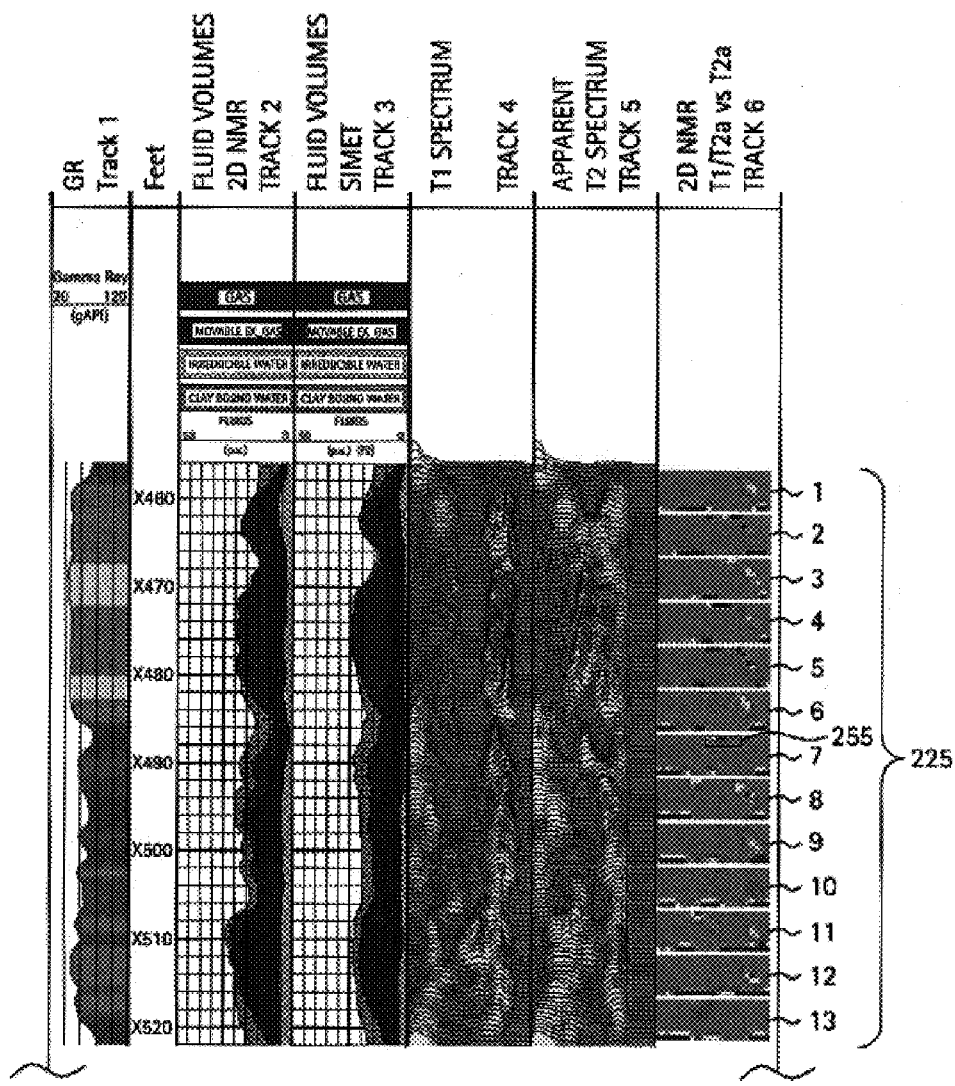
FIG. 9 depicts in log form 2D NMR images similar to those of FIGS. 4A and 4B in accordance with an embodiment of the invention.

An exemplary embodiment of the invention also includes a 2D display of a NMR image of R vs. $T_{2app}$ in log form, which will now be discussed with reference to FIG. 9. As used herein, the term log form refers to a series of several displays of NMR data relative to the depth of the logging tool, with each display being referred to as a track. In FIG. 9, tracks 1-6 of a NMR log are illustrated, with tracks 1-5 displaying typical readouts known in the well logging industry, and track 6 displaying a series of maps 225 in accordance with an embodiment of the invention. Here, the individual images (maps) of R vs. $T_{2app}$ (herein also referred to as frames) are separated by a white line, with each image representing the data corresponding to the middle of the actual depth interval defined by the distance between the two white lines. However, embodiments of the invention are not limited to displaying only the middle data, and may also include the display of other analytical results performed on the data from the depth interval, such as an averaged value for example. By providing a 2D NMR map of R vs. $T_{2app}$ in log form, one can readily identify the presence of a light hydrocarbon signal in the region 165, as depicted by the boxed portion 255 in frame-7 of the series of maps 225 on track 6 of FIG. 9.

As discussed previously, an embodiment of apparatus 100 may include processing circuit 120 and storage medium 125, where storage medium 125 is readable by processing circuit 120 and stores instructions for execution by processing circuit 120 for performing the method 300 according to the previously discussed embodiments. However, it will be appreciated that the processing of the data logged by apparatus 100 may or may not occur locally. For example, an embodiment of the invention may include a local storage medium 125 at apparatus 100, but a remote processing circuit 120 at surface equipment 150. Another embodiment of the invention may include a remote storage medium 125 and a remote processing circuit 120 at surface equipment 150, with a communication link via a hardwire (not shown) running alongside cable 135 for example, or via a wireless communication scheme. Accordingly, embodiments of the invention are not limited to local processing of the acquired data.

In view of the foregoing, embodiments of the invention may be embodied in the form of computer-implemented processes and apparatuses for practicing those processes. Other embodiments of the invention may be embodied in the form of computer program code containing instructions embodied in tangible media, such as floppy diskettes, CD-ROMs, hard drives, or any other computer readable storage medium that may provide a computer program product, wherein, when the computer program code is loaded into and executed by a computer, the computer becomes an apparatus for practicing the invention. Further embodiments of the invention may be embodied in the form of computer program code, for example, whether stored in a storage medium, loaded into and/or executed by a computer, or transmitted over some transmission medium, such as over electrical wiring or cabling, through fiber optics, or via electromagnetic radiation, wherein, when the computer program code is loaded into and executed by a computer, the computer becomes an apparatus for practicing the invention. Where implemented on a general-purpose microprocessor, the computer program code segments configure the microprocessor to create specific logic circuits. The technical effect of the executable instructions is to generate a $g(T_{2app}, R)$ signal intensity map characteristic of the nuclei at a subterranean region to identify a gas-bearing zone in the region in response to the location of a high-intensity signal on the map.

While the invention has been described with reference to exemplary embodiments, it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof. Therefore, it is intended that the invention not be limited to the particular embodiment disclosed as the best or only mode contemplated for carrying out this invention, but that the invention will include all embodiments falling within the scope of the appended claims. Moreover, the use of the terms first, second, etc. do not denote any order or importance, but rather the terms first, second, etc. are used to distinguish one element from another. Furthermore, the use of the terms a, an, etc. do not denote a limitation of quantity, but rather denote the presence of at least one of the referenced item.

What is claimed is:

1. A method for obtaining a parameter of interest relating to a region investigated by utilizing a nuclear magnetic resonance (NMR) tool capable of generating a magnetic field B and a pulse sequence suitable for investigating the region, the tool being responsive to a magnetic field gradient G, the nuclei of the region being subjected to the pulse sequence, the nuclei of the region characteristically having a longitudinal relaxation time $T_1$ distribution and an apparent transverse relaxation time $T_{2app}$ distribution, the NMR tool being capable of producing NMR data responsive to the nuclei, wherein the method comprising:

in response to the produced NMR data, defining an R distribution in a processor as a function of $T_1/T_{2app}$, processing in independent bins within the processor the $T_{2app}$ and R distributions along with the produced NMR data according to an inversion model, providing a signal intensity map of R versus $T_{2app}$ that is representative of the parameter of interest, and subsequently in response to a defined-intensity signal on the map where $T_{2app}$ and R are each confined, respectively, within defined ranges, identifying the parameter of interest within the region; and wherein a recording of the signal intensity map occurs in or on a recordable medium for use by an end user.

2. The method of claim 1, wherein:

the $T_{2app}$ range comprises a first $T_{2app}$ threshold value of 16 milliseconds (msec) and a second $T_{2app}$ threshold value of 256 msec; and the R range comprises an R value equal to or greater than 10.

3. The method of claim 1, wherein:

the NMR tool is capable of generating a magnetic field gradient G of about 30 Gauss/cm, and an echo time spacing TE of about 1 msec.

4. The method of claim 1, further comprising:

in response to a defined-intensity signal on the map having an R value equal to or greater than but substantially close to 1, identifying via the recorded map the presence of a liquid phase substance within the region.

5. The method of claim 1, further comprising:

defining a cutoff value Rc such that defined-intensity signals having a value of R greater than Rc are categorized as light hydrocarbon signals and defined-intensity signals having a value of R less than Rc are categorized as liquid phase signals.

6. The method of claim 5, further comprising:

determining an apparent volume of gas in the region by summing up the light hydrocarbon signal intensities in the map domain defined by R equal to or greater than Rc; and determining an actual volume of gas in the region by applying a gas hydrogen index correction to the apparent gas volume, thereby defining an HI corrected pore volume.

7. The method of claim 5, further comprising:

determining a liquid phase pore volume in the region by summing up the signal intensities in the map domain defined by R less than Rc;

determining a total porosity in the region by summing the HI corrected pore volume with the liquid pore volume; and determining a gas saturation as being a function of the HI corrected pore volume and the total porosity.

8. The method of claim 1, wherein the signal intensity map comprises cells that represent signal intensities as a function Of $T_{2app}$ and R, and further comprising:

determining a one-dimensional $T_{2app}$ distribution by summing up the two-dimensional intensity map in a vertical manner with respect to the $T_{2app}$ axis; and determining a one-dimensional $T_1$ distribution by summing up the two-dimensional intensity map from the $T_{2app}$ axis in a diagonal manner toward the R axis.

9. The method of claim 8, further comprising:

reconstructing in or on a storage medium the one-dimensional $T_{2app}$ and $T_1$ distributions to logs in response to the distributions having been determined on a depth by depth basis.

10. The method of claim 8, further comprising:

in response to a defined-intensity signal having a $T_{2app}$ relaxation time less than about 512 msec, and a $T_1$ relaxation time equal to or greater than about 512 msec and equal to or less than about 8192 msec, identifying the presence of a gas-bearing zone in the region via the recorded map.

11. The method of claim 10, wherein:

the identifying the presence of a gas-bearing zone comprises identifying retrograde condensates and dry gases by different map signatures presentable to the end user via the recorded map.

12. The method of claim 1, further comprising:

applying a regularized non-negative least squares formulation to the inversion model for the purpose of reducing random noise effects and for providing a smoother curve fit of model to data.

13. The method of claim 8, further comprising:

constraining the sum of the two-dimensional intensity map in the vertical direction with respect to the $T_{2app}$ axis to be the same as a corresponding standard one-dimensional $T_{2app}$ distribution.

14. The method of claim 1, wherein the applied two-dimensional inversion model is in accordance with the following equation:

$$M = \int_1^\infty \int_0^\infty g(T_{2app}, R)\left(1 - e^{-\frac{TW}{R \cdot T_{2app}}}\right) e^{-\frac{t}{T_{2app}}} dT_{2app} dR,$$

where:
M represents the NMR echo data,
t represents the time between adjacent echoes multiplied by an echo index,
TW represents the wait time, and
$g(T_{2app}, R)$ represents the solution map.

15. A computer program product comprising a computer readable medium having computer readable program code means embodied in the medium, the computer readable program code means capable of implementing the method of claim 14.

16. The method of claim 1, further comprising:
displaying on a display a series of 2D NMR images of R vs. $T_{2app}$ in log form.

17. A computer program product comprising a computer readable medium having computer readable program code means embodied in the medium, the computer readable program code means capable of implementing the method of claim 16.

18. The method of claim 1, wherein:
the magnetic field gradient G is intrinsic to the NMR tool.

19. The method of claim 2, wherein:
the R range comprises an R value equal to or less than 16.

20. The method of claim 1, wherein:
the defined-intensity signal is a high-intensity signal.

21. A nuclear magnetic resonance (NMR) apparatus configured for detecting and quantifying a parameter of interest in a region, the apparatus comprising:
a field gradient generator capable of applying a magnetic field gradient to the region;
a signal generator capable of applying a sequence of magnetic pulses to the region;
a signal receiver capable of receiving information from nuclei in the region responsive to the magnetic field gradient and the magnetic pulses;
a processing circuit configured to process the received information; and
a storage medium, readable by the processing circuit, storing instructions for execution by the processing circuit for:
receiving NMR data relating to the region;
in response to the received NMR data, defining an R distribution within the processing circuit as a function of $T_1/T_{2app}$, processing in independent bins within the processing circuit the $T_{2app}$ and R distributions along with the received NMR data according to an inversion model, and generating a signal intensity map of R versus $T_{2app}$ that is characteristic of the nuclei in the region;
recording the signal intensity map in or on a recordable medium for use by the processing circuit;
signifying the presence of a gas-bearing zone in the region in response to a defined-intensity signal occurring on the map being within a first range of $T_{2app}$ values and within a first range of R values; and
signifying the presence of a liquid phase substance in the region in response to a defined-intensity signal occurring on the map having an R value equal to or greater than but substantially close to 1 for any value of $T_{2app}$.

22. The apparatus of claim 21, wherein the storage medium further stores instructions for execution by the processing circuit for:
displaying a series of 2D NMR images of R vs. $T_{2app}$ in log form.

23. The apparatus of claim 21, wherein:
the field gradient generator is capable of applying a static magnetic field gradient.

24. A method for detecting and quantifying a parameter of interest in a region investigated by utilizing a nuclear magnetic resonance (NMR) tool capable of generating a magnetic field and a pulse sequence suitable, for investigating the region, the tool being responsive to a field gradient G, the nuclei of the region being subjected to the pulse sequence, the nuclei of the region characteristically having a longitudinal relaxation time $T_1$ distribution and an apparent transverse relaxation time $T_{2app}$ distribution, the NMR tool being capable of producing NMR data responsive to the nuclei, wherein the method comprising:
acquiring the NMR data;
in response to the acquired NMR data, defining an R distribution in a processor as a function of $T_1/T_{2app}$, processing in independent bins within the processor the $T_{2app}$ and R distributions along with the acquired NMR data according to an inversion model, and subsequently providing a signal intensity map of R versus $T_{2app}$ that is characteristic of the nuclei in the region;
recording the signal intensity map in or on a recordable medium for use by an end user; and
identifying a gas-bearing zone in the region in response to the location of a defined-intensity signal occurring on the map;
wherein a light hydrocarbon signal is represented on the map by a defined-intensity signal occurring in a first range of R values and a first range of $T_{2app}$ values; and
wherein a liquid phase signal is represented on the map by a defined-intensity signal occurring in a second range of R values and a second range of $T_{2app}$ values.

* * * * *